United States Patent [19]
Znaiden et al.

[11] Patent Number: 5,614,511
[45] Date of Patent: Mar. 25, 1997

US005614511A

[54] COSMETIC COMPOSITIONS FOR TREATING ITCHY SKIN

[75] Inventors: Alexander P. Znaiden, Trumbull; Brian A. Crotty, Branford; Anthony W. Johnson, Fairfield, all of Conn.

[73] Assignee: Chesebrough-Pond's USA Co., Division of Conopco, Inc., Greenwich, Conn.

[21] Appl. No.: 616,053

[22] Filed: Mar. 11, 1996

[51] Int. Cl.⁶ ........................................... A61K 31/66
[52] U.S. Cl. ........................................... 514/103
[58] Field of Search ........................... 514/23, 103

[56] References Cited

U.S. PATENT DOCUMENTS

| | | | |
|---|---|---|---|
| 4,112,073 | 9/1978 | Ono | 424/177 |
| 5,015,634 | 5/1991 | Siren | 514/103 |
| 5,019,566 | 5/1991 | Siren | 514/103 |
| 5,023,248 | 6/1991 | Siren | 514/103 |
| 5,051,411 | 9/1991 | Siren | 514/103 |
| 5,059,594 | 10/1991 | Sawai et al. | 514/103 |
| 5,082,833 | 1/1992 | Shamsuddin | 514/103 |
| 5,116,605 | 5/1992 | Alt | 424/70 |
| 5,268,176 | 12/1993 | Znaiden et al. | 514/103 |
| 5,300,289 | 4/1994 | Garlich et al. | 424/54 |
| 5,407,677 | 4/1995 | Tominaga et al. | 424/401 |
| 5,434,144 | 7/1995 | Kasting et al. | 514/103 |
| 5,476,853 | 12/1995 | Cauwenbergh | 514/253 |

FOREIGN PATENT DOCUMENTS 4242876  12/1992  Germany.

*Primary Examiner*—Raymond Henley, III
*Attorney, Agent, or Firm*—Milton L. Honig

[57] ABSTRACT

The invention is directed to controlling and alleviating itchiness of human skin. Itchiness is treated with a composition that includes inositol phosphate, particularly phytic acid and its salts, in a cosmetically acceptable carrier.

4 Claims, No Drawings

COSMETIC COMPOSITIONS FOR TREATING ITCHY SKIN

BACKGROUND OF THE INVENTION

1. Field of the Invention

The invention concerns a method for relieving itchiness in human skin.

2. The Related Art

A wealth of literature surrounds the beneficial chemistry of inositol phosphate. Most of this literature focuses upon the medicinal aspects involving oral ingestion of the material. For instance, U. S. Pat. No. 5,051,411 (Siren) utilizes inositol phosphates to reduce the negative effects of ingested toxic metals such as lead, mercury, nickel and chromium to prevent or alleviate disorders based upon such metals. Typical disorders disclosed were immunodeficiency, hypertension and dermatitis. Related disclosures are found in U. S. Pat. No. 5,015,634 (Siren) directed at preventing or alleviating tissue damage and U. S. Pat. No. 5,019,566 (Siren) directed at treating an inflammatory condition, such as arthritis. U. S. Pat. No. 5,023,248 (Siren) describes methods for treating diabetes or its complications by administration of inositol triphosphate.

U. S. Pat. No. 5,082,833 (Shamsuddin) discloses a method for moderating the rate of cellular mitosis by treatment with inositol phosphates. Target diseases are leukemia, AIDS and fungal or protozoal infections.

U. S. Pat. No. 5,059,594 (Sawai et al.) reports the use of phytic acid and ferric ions in compositions directed at the removal of uraroma and body smell, detoxication, treatment of diabetes and hyperlipemia, remediation of erythrocyte flexibility and dysmnesia and the inhibition of the proliferation of fat cells.

A much smaller body of literature has suggested the use of inositol phosphates such as phytic acid in the cosmetics area. For instance, U. S. Pat. No. 5,116,605 (Alt) incorporates phytic acid with a variety of other substances into a composition for mitigating male pattern baldness and testosterone-induced acne. U. S. Pat. No. 5,268,176 (Znaiden et al.) reports the use of phytic acid for topical treatment of telangiectasia, a dermatological condition commonly known as spider veins. A considerable number of disclosures are related to the use of phytic acid as a dental care product, among the more recent being U. S. Pat. No. 5,300,289 (Garlich et al.).

While it is evident from the foregoing that inositol phosphates are useful in a broad range of medical treatments, knowledge about their cosmetic activities is still at a formative stage.

Accordingly, it is an object of the present invention to describe new uses for inositol phosphates in the cosmetics area.

SUMMARY OF THE INVENTION

A method is provided for relieving itchiness in skin by applying onto the affected skin inositol phosphates in a pharmaceutically acceptable carrier.

DETAILED DESCRIPTION OF THE INVENTION

Now it has been found that inositol phosphates have utility in controlling, reducing and inhibiting the irritation of itchy human skin.

Accordingly, the method of the present invention requires a phosphate derivative of inositol, which may be one or a combination of a mono-, di-, tri-, tetra-, penta- or hexaphosphate of inositol. Inositol is also known as 1,2,3,4,5,6-hexahydroxycyclohexane and 1,2,3,4,5,6-cyclohexanehexol. Most preferred is inositol hexaphosphate, otherwise known as phytic acid. For further descriptions of these phosphates, attention is drawn to U. S. Pat. No. 5,051,411, herein incorporated by reference. Amounts of these phosphates may range anywhere from about 0.001 to about 40%, preferably from about 0.1 to about 20%, optimally from about 0.5 to about 10% by weight of the total composition.

Compositions of the present invention will also contain a cosmetically acceptable carrier for the inositol phosphate. Amounts of the carrier may range from about 60% to about 99.9%, preferably from about 80 to 99.5% by weight of the total composition. Included among the cosmetically acceptable carriers are emollients, surfactants, humectants, powders and water.

Preferably compositions of the present invention are emulsions of either the oil-in-water or water-in-oil or duplex variety. Relative amounts of oil phase to water phase may range from 1000:1 to 1:1000, preferably from 10:1 to 1:10.

A variety of oily emollients may be employed in the compositions of this invention. These emollients may be selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.

2. Acetoglyceride esters, such as acetylated monoglycerides.

3. Ethoxylated glycerides, such as ethoxylated glyceryl monostearate.

4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

7. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.

8. Fatty alcohol ethers. Ethoxylated fatty alcohols of 10 to 20 carbon atoms including the lauryl, cetyl, stearyl, isostearyl, oleyl, and cholesterol alcohols, having attached thereto from 1 to 50 ethylene oxide groups or 1 to 50 propylene oxide groups.

9. Ether-esters such as fatty acid esters of ethoxylated fatty alcohols.

10. Lanolin and derivatives, Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

11. Polyhydric alcohol esters. Ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

12. Wax esters such as beeswax, spermaceti, myristyl myristate, stearyl stearate.

13. Beeswax derivatives, e.g. polyoxyethylene sorbitol beeswax. These are reaction products of beeswax with ethoxylated sorbitol of varying ethylene oxide content, forming a mixture of ether esters.

14. Vegetable waxes including carnauba and candelilla waxes.

15. Phospholipids such as lecithin and derivatives.

16. Sterol including cholesterol and cholesterol fatty acid esters.

17. Amides such as fatty acid amides, ethoxylated fatty acid amides, solid fatty acid alkanolamides.

Amounts of the above listed emollients may range anywhere from about 0.5 to about 40% by weight of the total composition. Preferably the amounts of these emollients will range from about 2 to about 25%, optimally between about 5 and 15% by weight.

Humectants of the polyhydric alcohol-type may also be included in the compositions of this invention. The humectant aids in increasing the effectiveness of the emollients and reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range from about 0.5 to about 30%, preferably between 1 and 15% by weight of the composition.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include dimethyl polysiloxane (CTFA name: dimethicone), a polysiloxane endblocked with trimethyl units and polydimethylcyclosiloxane (CTFA name: cyclomethicone). The preferred siloxanes exhibit a viscosity from about 2 to 50 centistokes at 25° C. Amounts of the silicones can range from about 0.5 to about 50% by weight of the compositions, preferably from about 1 to about 10% by weight.

Surfactants can also be included in the compositions of this invention. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as cocoamidopropyl betaine).

Among the powders may be mentioned such materials such as chalk, talc, Fullers Earth, kaolin, starch and chemically modified starches, gums, colloidal silicon dioxide, sodium polyacrylate, tetraalkyl and/or trialkyl aryl ammonium smectites, chemically modified magnesium aluminum silicate, organically modified montmorillonite clay, hydrated aluminum silicate, fumed silica, sodium carboxymethyl cellulose, alkyl cellulose, zeolite, clays and combinations thereof. Amounts of these powders may range anywhere from about 1 to about 90% by weight of the composition.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Amounts of water in the composition may range anywhere from about 1 to about 99%, preferably from about 20 to about 90%, optimally between about 40 and 70% by weight.

Minor adjunct ingredients may also be included such as fragrances, antifoam agents, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A clinical study is herein reported which assesses the effect of inositol phosphate on itchy skin.

A group of 10 people were recruited for a week of home use of two products. All subjects were questioned as to their experience of itch. Only those who answered in the affirmative about current itch on the arms and or legs were included. Each panelist used two products, product A on left leg/arm/back of hand and product B on right leg/arm/back of hand. Panelists were told to apply products twice a day, once in the morning and once in the evening before bed. Panelists were told that they could continue their normal activities which brought them into contact with water except they should not use any other skin care products afterwards.

During the study, panelists were asked to make daily assessments of their skin and itch level using the provided diary forms. The first skin assessment was done before product use was started. The provided diaries included areas for panelists to rate itch on a scale of 0–100 throughout the study.

TABLE I

| COMPONENT | WEIGHT % A | WEIGHT % B |
|---|---|---|
| Inositol Phosphate (50% Solution) | 16.00 | — |
| Sodium Hydroxide (50% Solution) | 5.73 | — |
| Protachem ISP ® | 6.00 | 6.00 |
| Kikui Oil | 5.00 | 5.00 |
| Stearic Acid | 3.00 | 3.00 |
| Butylene Glycol | 3.00 | 3.00 |
| Hetester FAO ® | 3.00 | 3.00 |
| Glycerin | 2.00 | 2.00 |
| MYRJ 59 ® | 2.00 | 2.00 |
| Cholesterol | 1.50 | 1.50 |
| Naturechem GMHS ® | 1.50 | 1.50 |
| Stearyl Alcohol | 1.50 | 1.50 |
| Triethanolamine | 1.20 | 1.20 |
| Silicone Fluid 50 | 1.00 | 1.00 |
| Arlacel 60 ® | 1.00 | 1.00 |
| Emulmetik 300 ® | 0.75 | 0.75 |
| Veegum Ultra ® | 0.60 | 0.60 |
| Natrosol 250HHR ® | 0.50 | 0.50 |
| Cholesterol | 0.50 | 0.50 |
| Disodium EDTA | 0.50 | 0.50 |
| BHT | 0.50 | 0.50 |
| Xanthan Gum | 0.20 | 0.20 |
| Methylparaben | 0.15 | 0.15 |
| Antifoam Emulsion | 0.10 | 0.10 |
| Propylparaben | 0.10 | 0.10 |
| Water | to 100 | to 100 |

TABLE II

TEST RESULTS FORMULATIONS

| PREFERENCE | ITCH REDUCTION |
|---|---|
| Prefer Lotion A | 8* |
| Prefer Lotion B | 1 |
| No Preference | 1 |

*Final diary ratings were not used to judge itch reduction on two panelists because they reported both creams reduced their itch to zero by the end of the study. In these two cases, Lotion A was judged better than Lotion B because the former reduced itching faster than the latter.

Based on the results listed in Table II, it is evident that itch reductions were seen by a substantial majority of the panelists using Lotion A compared to those using the control (Lotion B). Accordingly, inositol phosphate was seen to have a significant effect upon reduction of itch.

EXAMPLE 2

An illustrative lotion containing sodium inositol phosphate for relief against itching is described in the formulation below.

| COMPONENT | WEIGHT % |
|---|---|
| Glycerin | 20.0 |
| Mineral Oil | 10.0 |
| Glycerol Monostearate | 10.0 |
| Sodium Inositol Phosphate | 8.0 |
| Salicylic Acid | 3.0 |
| Zinc Oxide | 2.0 |
| Bentonite | 2.0 |
| Water | balance |

EXAMPLE 3

An illustrative powder composition containing inositol phosphate for relief against itching is described in the formulation below.

| COMPONENT | WEIGHT % |
|---|---|
| Talc | 76.0 |
| Starch | 10.0 |
| Boric Acid | 6.0 |
| Inositol Phosphate | 3.0 |
| Zinc Stearate | 3.0 |
| Salicylic Acid | 2.0 |

EXAMPLE 4

A further illustrative composition, including the triethanolamine salt of inositol phosphate according to the present invention, is described below.

| COMPONENT | WEIGHT % |
|---|---|
| Silicone Oil | 6.0 |
| TEA Inositol Phosphate | 4.5 |
| Glyceryl Stearate | 4.0 |
| PEG 100 Stearate | 4.0 |
| Glycerin | 4.0 |
| $C_{12}$–$C_{15}$ Alcohol Benzoate | 3.5 |
| Lanolin | 3.5 |
| Squalene | 2.7 |
| Magnesium Aluminum Silicate | 0.4 |
| Methyl Paraben | 0.3 |
| Propyl Paraben | 0.2 |
| Carbopol 934 ® | 0.2 |
| Water | balance |

The foregoing description and Examples illustrate select embodiments of the present invention. In light thereof, various modifications will be suggested to one skilled in the art, all of which are within the purview and spirit of this invention.

What is claimed is:

1. A method for alleviating itching in human skin comprising topically applying to the skin a cosmetic composition consisting essentially of from about 0.1 to about 40% by weight of phytic acid and from about 60 to about 99.9% by weight of a cosmetically acceptable carrier.

2. A method according to claim 1 wherein the cosmetic composition is an oil and water emulsion.

3. A method according to claim 2 wherein the emulsion is a lotion or cream.

4. A method for alleviating itching in human skin comprising topically applying to the skin a cosmetic composition consisting essentially of from about 0.1 to about 40% by weight of a water-soluble salt of phytic acid selected from the group consisting of alkali metal, alkaline earth metal, ammonium and $C_2$–$C_{12}$ alkanolammonium salts and from about 60 to about 99.9% by weight of a cosmetically acceptable carrier.

* * * * *